US 6,706,011 B1

(12) United States Patent
Murphy-Chutorian et al.

(10) Patent No.: US 6,706,011 B1
(45) Date of Patent: *Mar. 16, 2004

(54) LASER ASSISTED DRUG DELIVERY

(76) Inventors: Douglas Murphy-Chutorian, 275 Lowell Ave., Palo Alto, CA (US) 94371; Richard L. Mueller, 5605 Deyo La., Jackson, WY (US) 83001; Stuart D. Harman, 559 Weddell Dr., Sunnyvale, CA (US) 94089; Steve A. Daniel, 40874 Calido Pl., Fremont, CA (US) 94539; Larry Witham, 559 Weddell Dr., Sunnyvale, CA (US) 94089; Bruce Richardson, 1011 S. Winchester Blvd. B-110, San Jose, CA (US) 95128

( * ) Notice: Subject to any disclaimer, the term of this patent is extended or adjusted under 35 U.S.C. 154(b) by 0 days.

This patent is subject to a terminal disclaimer.

(21) Appl. No.: 09/288,251

(22) Filed: Apr. 8, 1999

Related U.S. Application Data (63) Continuation of application No. 08/773,872, filed on Dec. 27, 1996, now Pat. No. 5,925,012, which is a continuation of application No. 08/773,430, filed on Dec. 27, 1996.

(51) Int. Cl.[7] ............................................. A61M 31/00
(52) U.S. Cl. ............................. 604/60; 604/21; 604/63
(58) Field of Search ............................ 604/518, 57, 20, 604/59–64, 21, 49–53, 65–67, 30, 31

(56) References Cited

U.S. PATENT DOCUMENTS

| | | | | |
|---|---|---|---|---|
| 797,183 A | * | 8/1905 | Davis | 604/62 |
| 834,261 A | * | 10/1906 | Chambers | 604/62 |
| 4,451,253 A | * | 5/1984 | Harman | 604/60 |
| 4,658,817 A | | 4/1987 | Hardy | 128/303.1 |
| 4,846,171 A | | 7/1989 | Kauphusman et al. | |
| 5,246,437 A | | 9/1993 | Abela | |
| 5,380,316 A | | 1/1995 | Aita et al. | 606/7 |
| 5,386,837 A | | 2/1995 | Sterzer | 128/898 |
| 5,389,096 A | | 2/1995 | Aita et al. | 606/15 |
| 5,498,238 A | | 3/1996 | Shapland et al. | 604/53 |
| 5,571,151 A | | 11/1996 | Gregory | |
| 5,840,059 A | | 11/1998 | March et al. | 604/53 |
| 5,925,012 A | * | 7/1999 | Murphy-Chutorian et al. | 604/20 |
| 5,999,678 A | * | 12/1999 | Murphy-Chutorian et al. | 280/12.12 |

FOREIGN PATENT DOCUMENTS

| | | |
|---|---|---|
| EP | 0 515867 A2 | 12/1992 |
| WO | WO 96/35469 A1 | 11/1996 |
| WO | WO 98/19614 | 5/1998 |

* cited by examiner

*Primary Examiner*—Sharon Kennedy
*Assistant Examiner*—Michael M Thompson
(74) *Attorney, Agent, or Firm*—Gibson, Dunn & Crutcher LLP (57) ABSTRACT

A drug delivery apparatus for dispensing predetermined volumes of drug, drug solution or other substances into an opening, such as a TMR channel in the human heart, or other laser treated area within the human body, the apparatus consisting of a bifurcated needle with a laser inlet for guiding a laser delivery means, such as an optical fiber or fiber bundle, to adjacent a surface of the human heart or other body structure for creating an opening, such as a TMR channel, or other laser treated area thereon. A drug inlet is for receiving the drug and transmitting the drug to the TMR channel or other laser treated area. Optionally, a piercing tip and/or suction device assists in positioning the apparatus adjacent the tissue to be treated. Drug is dispensed by manually or automatically actuating a piston or syringe element. A method of use is also disclosed.

12 Claims, 8 Drawing Sheets

LASER ASSISTED DRUG DELIVERY

This application is a continuation of application Ser. No. 08/773,872, filed on Dec. 27, 1996, now U.S. Pat. No. 5,925,012 allowed.

RELATED APPLICATIONS

This application is a continuation to U.S. patent application Ser. No. 08/773,430 filed Dec. 27, 1996 filed concurrently herewith.

FIELD OF THE INVENTION

The present invention relates generally apparatus and methods for delivering predetermined formulations and amounts of drugs or other materials to portions of the body with the aid of laser energy. More particularly, the invention relates to apparatus and methods for delivering predetermined formulations and amounts of drugs, medications or other materials to selected portions of tissue in conjunction with surgical and/or percutaneous procedures such as laser-assisted transmyocardial revascularization (TMR) procedures.

BACKGROUND OF THE INVENTION

In the treatment of heart disease, one method of improving myocardial blood supply is called transmyocardial revascularization (TMR), the creation of channels in the myocardium of the heart. The procedure using needles in a form of surgical "myocardial acupuncture" has been used clinically since the 1960s. Deckelbaum. L. P., Cardiovascular Applications of Laser technology, *Lasers in Surgery and Medicine* 15:315–341 (1994). It is believed that the technique relieves ischemia by allowing blood to pass from the ventricle through the channels either directly into other vessels communicating with the channels or into myocardial sinusoids which connect to the myocardial microcirculation.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and remain patent. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

U.S. Pat. No. 5,389,096 issued Feb. 14, 1995 to Aita et al. purports to teach one method of percutaneous TMR using an elongated flexible lasing apparatus with control lines and a focusing lens structure at the distal tip. The method describes the use of pressure to attempt to stabilize the apparatus against the wall of the heart. None of the cited TMR prior art references suggest delivery of drugs with the TMR apparatus.

In the field of drug delivery, many techniques currently exist for delivering drugs or other materials to the human body. These include, among others, oral administration, injection directly into body tissue such as through an intramuscular injection, transcutaneous injection in which a compound is injected directly into the vasculature of a patient, or topical administration. Although many situations are satisfactorily treated by the general or directed, typically systemic acting administration of a drug, there are a great many treatments which could be facilitated and/or improved by the ability to deliver or administer a drug locally to a selected portion of a patient's body.

A recent patent, U.S. Pat. No. 5,498,238 issued Mar. 12, 1996 to Shapland et al., discloses a method of simultaneous angioplasty and drug delivery to localized portions of arteries. The patent teaches the use of an expandable balloon end type catheter which can be filled with a drug-containing fluid and which is allowed to permeate through a semi-permeable membrane of the balloon-tip end and thereby be delivered directly to the surface of arteriosclerotic lesions on stenosed arteries. However, the patent does not teach drug delivery in conjunction with any type of laser procedure nor does it contemplate such delivery with the aid of laser energy. Nor does it teach delivery of drugs or other materials directly into tissue located within portions of the body not otherwise directly accessible.

U.S. Pat. No. 5,386,837 to Sterzer discloses an "electro-chemotherapeutic" technique for treating tumors in which high intensity electromagnetic force fields (including a laser) are applied to the body after chemotherapy has been applied. This is intended to create large, transient pores in individual cells of a superficially-seated tumor lesion located between individually mounted ceramic horn antennae by non-invasively applying a highly directional beam of force-field shock of HF pulsed wave energy into the cells, thus inducing the drug to enter the cells. The patent does not, however, teach apparatus or methods for disposing such drugs or medications into the portion of the body to be treated, but instead relies on the standard approaches to chemotherapy drug delivery. The patent does not anticipate delivery of drugs to selected portions of myocardium in the heart or other internal organs of the body, but rather is directed to augmented chemotherapy to treat breast cancer and prostate cancer or benign prostatic hyperplasia (BPH).

There are a number of important problems that are not addressed by systems of the present art. None of the prior art teaches how to administer drugs from within the tissue to be treated thereby minimizing the amount of drug required, particularly for costly drugs, and also confining the drug or drugs to the particular part of the body or tissue of interest, with more importance in this regard for the administration of toxic drugs. These problems are addressed by the delivery of drugs to the tissue of internal organs, such as the heart, in conjunction with or assisted by laser energy delivery. In particular, with regard to TMR procedures, the use of laser energy combines the latest advances in the development of cardiac medications with the most advanced techniques of TMR in order to enhance and optimize treatment administered to the patient.

ADVANTAGES AND SUMMARY OF THE INVENTION

In general, this invention is directed to the delivery of drugs in any form in, near or around laser-created openings in structures including organs and other tissue within the human body, and more particularly, this invention is directed toward a system for delivering a drug directly into a channel formed in a target region of the body. The channel is created using essentially any medical laser system, particularly laser systems used in TMR procedures. While TMR procedures have been directed towards revascularization of the heart, it is understood that these principles underlying the devices and methods of use of this invention can be applied to other areas of the body. Therefore, in the context of this specification, the terms target area, target region and target surface include a patient's heart as well as any other portion of the body to which the practices of this invention can apply, including but not limited to other normal or abnormal tissue, tumors, organs, bones and muscle.

Thus, it is an advantage of the present invention to deliver drugs in all forms to laser-treated tissue.

It is a further advantage to provide an apparatus and method of use for delivering drugs to laser created channels or openings in the human body or on the surface of tissue, for instance surgical or percutaneous TMR sites, which overcome the drug delivery limitations of the prior art.

It is a further advantage of the present invention to deliver medication directly to a localized target region of the body, such as the heart, thereby enabling efficient, cost effective drug treatment and, in the case of highly toxic agents, reduction of damage to healthy tissue.

It is a further advantage of the present invention to provide a system of providing medication to tissue in which the time required for the medication to reach the tissue is reduced, inasmuch as success of such treatment in many situations depends on the medication being able to reach the tissue within a very short period of time.

Another advantage of such a system is the ability to administer a medication directly to target tissue or target areas at preselected times of delivery and rates of delivery.

Another advantage of such a system is the ability to administer saline or flushing solutions directly to target tissue or target areas at preselected times of delivery and rates of delivery.

It is a further advantage of such system to provide means to control not only the rate of delivery but also the composition of the drug or other substance solution according to a control protocol, optionally including capability to modify the administration of such drugs based on vital measurements of patient parameters such as pulse rate, blood pressure or body temperature, etc.

It is yet a further advantage of the present invention to provide a surgical or catheter apparatus which can be positioned securely adjacent a target region in a portion of the vasculature or other organ, including portions of myocardium, to be treated with drugs using laser energy.

A further advantage of the present invention is to provide such apparatus to enable drug delivery in conjunction with, i.e. before, during or after, creation of one or more laser-created openings or channels on or in selected target surfaces within the body quickly and safely.

Additionally, a more specific advantage is to provide drug delivery before, during or after laser creation of TMR channels extending through the myocardium, blind channels extending into but not through myocardium, stimulation pockets within myocardium, and other stimulation zones created using laser energy to stimulate angiogenesis.

In a preferred embodiment of the present invention, the apparatus includes a laser delivery means and one or more conduits transmitting drug, the laser delivery means and the one or more drug conduits coming together in a manifold means to direct both, simultaneously or alternatingly, to the target region. The conduits transmitting the drug are separate from the laser delivery means and both are guided into branches of a needle or tube-type manifold. In use, the laser delivery means is extended through a first branch and a common tube of the manifold to the target surface and the laser energy is delivered to form a channel or opening or otherwise act thereon. The drug is transmitted through a second branch and the common tube prior to, simultaneous with or subsequent to formation of the opening or channel. A pointed tube may be mounted on the distal end of the laser delivery means, or the laser delivery means may have a sharpened distal tip, which pierces the target surface prior to applying the laser beam.

Several constructions are contemplated for positioning the target end of the laser delivery means and then transmitting the drug. Construction of the apparatus could include, for example, in a preferred embodiment, a housing which contains one or more syringes whose plungers are controlled manually or automatically. Control of the transmission of drug is exercised by the operator depressing a switch or plunger to dispense drugs into the one or more branches of a needle or other tube-type manifold. The laser delivery means extends through the housing and is extended or retracted by advance means, such as by tuning a thumbwheel in the housing. Adjustable parameters of such handheld apparatus include switches for activating and controlling delivery of drugs, setting aliquot dosage, repetition rate, etc.

In a preferred method of the present invention, a laser beam from the end of the laser delivery means creates a TMR channel or other opening in the target region. In a second step, which could be performed prior to or simultaneously with the first step, the drug is transmitted through the conduit directly into the TMR channel or other opening. In an optional step, which could either be performed prior to or simultaneously with the first and/or the second steps, the target surface, such as epicardium or endocardium, is pierced with a mechanical piercing means to provide initial access to the target region of tissue, such as myocardium. Delivery of drug ma of course, be accomplished after creation of the channel or opening. Additionally, suction may be provided at the target surface to stabilize the drug delivery and/or the laser apparatus.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Scope of Drug Delivery

The concept of drug delivery includes any application where a drug or other substance is delivered in the area of laser treatment. This invention relates generally to the topic of drug delivery with laser delivery devices, and more particularly to drug delivery in conjunction with TMR in which, for example, antiarrhythmic drugs, growth factors or other drugs or compounds can be delivered to the heart during the TMR procedure.

For the purposes of the present invention and disclosure herein, the term "drug" or "drugs" includes any and all drugs which could or will be used in the manners described herein, including and not limited to the compounds named in the following tables, other medications, antibiotics, vaccines, function regulators, other materials for performing functions including flushing and cooling, stimulating other responses, detection, analysis, monitoring, visualization or control, etc., said solutions comprising waters, saline and the like, solid and semi-solid materials, and in any forms including capsules and granules, implants, etc.

The present invention includes the delivery of liquid, solid or semi-solid, time release formulations, etc. It is important to consider that a large local concentration of drug may result, particularly in the case of when a solid dissolves in fluid or tissue and becomes bioavailable, unless the particular drugs or other substances being delivered are fairly insoluble or are otherwise formulated to dissolve slowly enough to avoid unacceptably high concentrations, locally or elsewhere. Care must also be taken to avoid solid materials drifting or migrating from the area of intended treatment, such as by implantation, transdermal application, etc.

Preferred parameters for drug delivery in conjunction through a laser catheter provide a single, acute or multiple acute or sustained administration of the drug to produce a therapeutic effect. Additionally, for certain drug systems, drug half-life should be consistent with the clearance mechanisms present in the environment where the drug is introduced. Drugs that need frequently repeated administration over longer periods of time could require repeated hospitalizations or clinic visits—an exception to this is in the case of cancer chemotherapy, where the patient normally goes to the hospital for drug administration in the course of routine treatment. In the case of a drug administered with TMR, where blood circulation may cause a rapid clearance of any therapeutic delivered in or near the channels, the drug would need a time course of action that is rapid enough to have effect before it is cleared.

One set of applications of such drug delivery in conjunction with laser procedures involve certain antibody treatments, where it is desirable to target the antibody to the area of intended treatment in order to achieve the highest possible local concentration of a relatively extremely expensive reagent. For example, in enzyme-linked antibody therapy currently under investigation in the treatment of certain cancers, an enzyme linked to an antibody specific to a tumor is delivered and allowed to bind to the tumor cells.

Thus, at present the two main applications for which laser assisted drug delivery would be advantageous are (1) delivery of angiogenic factors in conjunction with TMR and (2) delivery of a chemotherapeutic to a solid tumor after a laser is used to ablate tumor tissue. A normally toxic chemotherapeutic such as doxorubicin or taxol that is made systemically non-toxic by being modified to a prodrug is injected into the tumor. The drug would remain non-toxic until it meets the enzyme linked to the antibody, where the prodrug is converted into active drug. In this way, higher local concentrations of the drug could be created near the tumor than would be possible by traditional chemotherapy, where systemic toxicity is the limiting factor.

Scope of Drug Therapy

Therapeutics which may be advantageous to deliver through a laser/catheter device can be broadly placed into four overlapping therapeutic categories:

1) agents which act on the blood clot cascade,
2) agents that mediate inflammation or cell adhesion/ recognition processes,
3) agents which have an effect on the cardiovascular system, and
4) agents that may be used in the treatment of cancer.

These categories are broadly overlapping, so that many agents will fall into more than one category. Antibody agents, for example, will appear in all four categories. Certain growth inhibitors can be used for anti-cancer treatment as well as for the treatment of other disease processes. Agents named in the following charts are illustrative and are not meant to be a comprehensive listing of all agents available for the given therapeutic category. Agents appearing as examples in one category may have uses in other therapeutic categories.

It will be understood that there are additional categories which may become useful, such as agents which are directed at bone, agents implanted in semi-permeable sacs, radioisotopes, and future gene therapies.

Photodynamic therapy is another important delivery and dosing method. Drugs or other compounds which have certain therapeutic or other activity or function can be regulated using such technology. Photo-active or photo-labile compounds are those whose activity or function is controlled by light energy. While the use of sensitizing agents or protective groups to block activity of the drug or other compounds in topically applied formulations is known, the use of such protective groups is unknown in conjunction with drugs delivered for angiogenic purposes or in conjunction with TMR.

"Caged" compounds are compounds which have a photoactive reagent which masks the original characteristics of the compounds. Thus, these caged or otherwise photo-labile compounds can be delivered to the target tissue or target region in a pharmacologically in-active form. Upon irradiation with laser energy or other, operative electromagnetic radiation, the protective group or groups are caused to be rendered inert, thereby initiating therapeutic activity. These photoactive protective groups or "cage" molecules are especially useful in conjunction with highly toxic drugs or marker substances. For example, chemotherapeutic agents are particularly toxic and, thus, their toxicity can be eliminated until the agent is delivered to the precise region of the body where it's toxicity will be most effectively and safely used. Irradiation of the photo-labile compound with light energy of a suitable wavelength, frequency and duration can then render the drug or other photo-labile agent active.

Dosing

Active compounds which are given systemically have a normal therapeutic window which can be expressed as mg of drug per kg of body weight. The amount of agent which is therapeutically acceptable when administering a drug locally can be approximated as mg of drug per kg of target treatment area (e.g. organ weight), optimized accordingly with consideration of toxicity and mechanism of drug action.

Agents delivered to a specific site can achieve high local concentrations at the delivery point. Optimal drug dose may scale differently when the drug is administered locally rather than systemically. Thus, the amount of a given agent that should be delivered in order to achieve a therapeutic effect must be optimized accordingly with consideration of toxicity levels (both locally and systemically), mechanism of drug action, drug clearance mechanisms, and drug diffusion levels.

Category 1—Examples of Agents Which Have an Effect on the Blood Clot Cascade

These agents work by either promoting or inhibiting blood clot cascade pathways. These agents are actual blood clot cascade participants, which mimic actual blot clot cascade participants, or agents which act as enzymes or inhibit enzymes that are associated with the blood clot cascade. Some examples of agents in these categories include:

| Category | Agent | Manufacturer | Indication | Form |
| --- | --- | --- | --- | --- |
| Anticoagutant Antagonists | Protamine Sulfate | Eli Lilly | treatment of heparin overdosage | IV |
| Anticoagulants | Heparin | Wyeth-Ayerst | prophylaxis and treatment of venous thrombosis; prevention of post-operative deep venous thrombosis and pulmonary embolism; prevention of clotting in arterial and cardiac surgery; prophylaxis and treatment of peripheral arterial embolism | IV |
| Antifibrinolytic | Amicar (aminocaproic acid) | Immunex | enhances hemostasis when fibrinolysis contributes to bleeding | IV/oral |
| Platelet Inhibitors | ReoPro (abciximab) | Eli Lilly | adjunct to percutaneous transluminal coronary angioplasty or atherectomy (PTCA) for the prevention of acute cardiac ischemic complications in patients at high risk for abrupt closure of the treated coronary vessel | IV |
| Thrombolytics | Activase (alteplase, TPA) | Genentech | management of acute myocardial infarction in adults, management of acute massive pulmonary embolism in adults | IV |

Category 2—Examples of Agents That Mediate Cell Adhesion and/or Cell Recognition Processes These agents act on cell signaling pathways and recognition processes, and includes receptor agonists and antagonists. A subset of these agents mediate inflammation and the immune response. Some examples of agents in the category include:

| Category | Agent | Manufacturer | Indication | Form |
| --- | --- | --- | --- | --- |
| Antihistamines | Seldane (terfenadine) | Marion Merrell Dow | relief of symptoms associated with seasonal allergic rhinitis | oral |
| Anti-Inflammatory Agents | Toradol (ketorolac tromethamine) | Roche Laboratories | short-term (<5 days) management of moderately severe, acute pain that requires analgesia at the opioid level | IV/IM/oral |
| Immunosuppressives | Sandimmune (cyclosporin) | Sandoz | prophylaxis of organ rejection in kidney, liver, and heart allogeneic transplants; also in the treatment of chronic rejection in patients previously treated with other immunosuppresive agents | IV/oral |
| Receptor Antagonists | Tagamet (cimetidine hydrochloride) | SmithKline Beecham | management of ulcers, erosive gastroesophageal reflux disease, prevention of upper gastrointestinal bleeding in critically ill patients, treatment of pathological hypersecretory conditions | IV/IM/oral |

Category 3—Examples of Cardiovascular Agents

These agents work at various points in the cardiovascular and associated systems. Angiogenic factors and anti-angiogenic factors appear in this category as well as in the cancer therapeutics category. Some examples of agents in the category include:

| Category | Agent Name | Manufacturer | Indication | Form |
|---|---|---|---|---|
| Adrenergic Blockers | Minipress (prazosin hydrochloride) | Pfizer | treatment of hypertension | oral |
| Adrenergic Stimulants | Aldomet (methyldopate HCl) | Merck | treatment of hypertensive crisis | IV |
| Alpha/Beta Adrenergic Blockers | Normodyne (labetalol HCl) | Schering | control of blood pressure in severe hypertension | IV |
| Angiotensin Converting Enzyme Inhibitors | Capoten (captopril) | Bristol-Myers Squibb | treatment of hypertension | oral |
| Angiotensin II Receptor Antagonists | Cozaar (losartan potassium) | Merck | treatment of hypertension | oral |
| Antiarrhythmics Group I | Norpace (disopyramide phosphate) | Searle | treatment of documented ventricular arrhythmias, such as sustained ventricular tachycardia | oral |
| Antiarrhythmics Group II | Brevibloc (esmolol hydrochloride) | Ohmeda | rapid control of ventricular rate in patients with atrial fibrillation or atrial flutter in perioperative, postoperative, or other emergent circumstances where short term control of ventricular rate with a short-acting agent is desired; indicated in noncompensatory sinus tachycardia where the rapid heart rate requires specific intervention; indicated of the treatment of tachycardia and hypertension that occur during induction and tracheal intubation, during surgery, on emergence from anesthesia, and in the postoperative period | IV |
| Antiarrhythmics Group III | Cordarone (amiodarone HCl) | Wyeth-Ayerst | treatment and prophylaxis of frequently recurring ventricular fibrillation and hemodynamically unstable ventricular tachycardia in patients refractory to other therapy | IV/oral |
| Antiarrhythmics Group IV | Cardizem (diltiazem HCl) | Marion Merrell Dow | IV: indicated for atrial fibrillation or atrial flutter and paroxysmal supraventricular tachycardia oral: treatment of hypertension and management of chronic stable angina and angina due to coronary artery spasm | IV/oral |
| Beta Blockers | Inderal (propranolol HCl) | Wyeth-Ayerst | management of hypertension, management of angina pectoris due to coronary atherosclerosis, management of cardiac arrhythmias, indicated to reduce cardiovascular mortality in patients who have survived the acute phase of myocardial infarction and are clinically stable, prophylaxis of the common migraine headache | IV/oral |
| Calcium Channel Blockers | Procardia (nifedipine) | Pratt Pharmaceuticals | management of vasospastic angina, chronic stable angina, and hypertension | oral |
| Diuretics | Bumex (bumetanide) | Roche | treatment of edema associated with congestive heart failure, hepatic and renal disease, including nephrotic syndrome | IV/IM/oral |
| Hypertensive Emergency Agents | Hyperstat (diazoxide) | Schering | short-term use in the emergency reduction of blood pressure in severe, non-malignant and malignant hypertension | IV |

| Category | Agent Name | Manufacturer | Indication | Form |
| --- | --- | --- | --- | --- |
| Growth Factors | Vascular Endothelial Growth Factor (VEGF) (preclinical) | Genentech | promotes angiogenesis; still experimental | pre-clinical |
| Inotropic Agents | Lanoxin (digoxin) | Glaxo Wellcome | management of heart failure, atrial fibrillation, atrial flutter, paroxysmal atrial tachycardia | IV/oral |
| Patent Ductus Arteriosus Therapy | Indocin (indomethacin sodium trihydrate) | Merck | indicated to close a hemodynamically significant patent ductus arteriosus in premature infants | IV |
| Rauwolfia Derivatives & Combinations | Diupres (reserpine-chlorothiazide) | Merck | hypertension | oral |
| Vasodilators | Nitrostat (nitroglycerin) | Parke-Davis | prophylaxis, treatment, and management of patients with angina pectoris | oral |
| Vasopressors | Vasoxyl (methoxamine hydrochloride | Glaxo Wellcome | supporting, restoring, or maintaining blood pressure during anesthesia | IV |

Category 4—Examples of Cancer Therapeutics

Cancer therapy can proceed along several different lines, all of which seek to kill or limit the growth of cancer cells while doing minimal damage to the host. Thus, any difference in cancer cell properties (e.g. metabolism, cell-surface antigen presentation) from healthy host cells is a target for exploitation. With the local administration of therapeutics, these differentiating factors may be created and/or exploited. For example, the local administration of cytotoxins or growth inhibitors may allow higher local concentrations of the compounds than would be achievable by systemic administration. Differences in cell-surface recognition molecules may be a site for antibody therapy. Differences in tumor morphology are also potential sites of intervention: for example, anti-VEGF may be useful in retarding the vascularization of the interior of a solid tumor, thereby slowing its growth rate. Some examples of agents in the category include:

| Category | Agent Name | Manufacturer | Indication | Form |
| --- | --- | --- | --- | --- |
| Adjuncts | Kytril (granisetron HCl) | SmithKline Beecham | prevention of nausea and vomiting associated with emetogenic cancer therapy, including high-dose cisplatin | IV |
| Androgen Inhibitors | Lupron (leuprolide actetate) | TAP Pharmaceuticals | palliative treatment of prostatic cancer | IM |
| Antibiotic Derivatives | Doxorubicin Hydrochloride | Astra USA | produces regression in disseminated neoplastic conditions and possibly some solid tumors | IV |
| Antiestrogen | Nolvadex (tamoxifen citrate) | Zeneca Pharmaceuticals | treatment of metastatic breast cancer | oral |
| Antimetabolites | Roferon-A (interferon alfa-2a) | Roche | treatment of hairy cell leukemia and AIDS-related Kaposi's sarcoma | IM/SC |
| Cytotoxic Agents | Taxol | Bristol-Myers Squibb | treatment of metastatic carcinoma of the ovary and treatment of breast cancer | IV |
| Enzyme Inhibitors | Ras farnesyl-transferase inhibitor (preclinical) | Genentech | treatment of pancreatic and colon cancers | pre-clinical |
| Hormones | Depo-Provera (medroxy-progesterone acetate) | Upjohn | adjunctive therapy and palliative treatment of inoperable, recurrent, and metastatic endometrial or renal carcinoma | IV |
| Immuno-modulators | Proleukin (aldesleukin) | Chiron | treatment of metastatic renal cell carcinoma | IV |
| Nitrogen Mustard Derivatives | Alkeran (melphalan HCl) | Glaxo Wellcome | treatment of multiple myeloma | IV/oral |

TMR and Angiogenic Factors

TMR is based on the theory that blood will flow directly from the left ventricle into the channels and then into the myocardial vascular plexus. Although the mechanism of TMR is still being investigated, there is some indication that the channels remain patent for a significant period of time following their creation. There is a question of whether blood washing in and out of the channels and the attendant diffusion into the muscle provides an adequate oxygen supply to the myocardium. The possibility exists that since TMR induces some secondary vascularization, whatever signal is given to induce vascularization could be pharmacologically amplified. Mechanisms for this type of induced revascularization may stem from factors induced by tissue damage (VEGF or other growth-factor derived response, or perhaps heat-shock proteins produced by thermal damage caused by the laser). Regardless of the actual mechanism, an angiogenic factor used in conjunction with TMR may increase the effectiveness of the technique.

A preferred one of the angiogenic factors commonly available (e.g. VEGF, FGF-1, FGF-2, EGF) is VEGF, vascular endothelial growth factor. VEGF has been shown to be effective in improving vascularization in the rabbit ischemic hindlimb model after a single bolus administration. VEGF also has a serum half life of less than 6 minutes (unpublished results), and certain isoforms of VEGF have the property to bind to the cell surface—i.e. VEGF may not need to be present for very long in order to have an effect. Thus, it is possible to apply VEGF in or near TMR channels to increase the revascularization of ischeric myocardium.

If the cause of ischemia is a constriction of blood supply upstream from the capillary bed, then VEGF therapy alone will not be shown to be as effective as TMR alone. Angiogenesis produced by VEGF in the myocardium may have limited effectiveness when the cause of ischemia is occlusion of coronary arteries: this limits the amount of blood available to the myocardium. The advantage of a TMR/VEGF combination treatment is that the transmural channels created in TMR could provide a source of blood to the newly vascularized myocardium that is otherwise unavailable.

Basic fibroblast growth factor (bFGF), also known as FGF-2, is another possible agent. There is some indication that VEGF and bFGF used together are more effective than either one alone.

Laser Assisted Drug Delivery Apparatus

For purposes of clarity, identical reference numerals are used throughout the accompanying drawings, corresponding to structurally and/or functionally similar elements of the invention disclosed herein.

Figure 1:
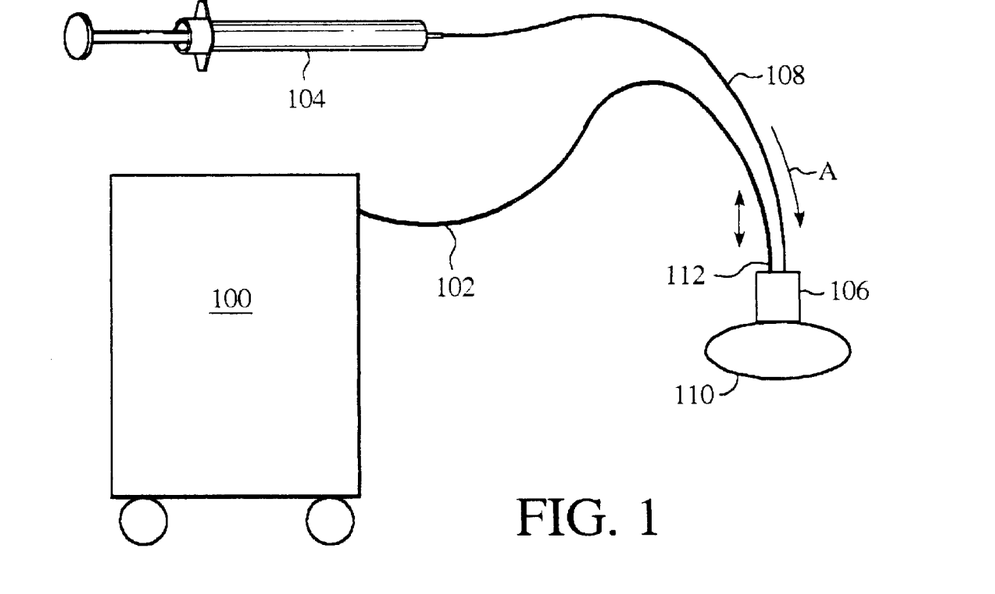
FIG. 1 is a representative schematic view of a preferred embodiment of the laser assisted drug delivery apparatus of the present invention.

FIG. 1 is a representative schematic view of a preferred embodiment of a laser delivery means adapted for drug delivery apparatus of the present invention. A laser source 100 provides laser energy. Laser energy is delivered via laser delivery means 102. It will be understood that said laser delivery means 102 can be any suitable laser delivery means including individual optical fibers, bundles of optical fibers, cables, rods, waveguides, articulating arms or other devices known to those skilled in the art. The drug reservoir and dispenser mechanism 104 dispenses drugs, solutions, solids, or other substances via drug conduit 108 to manifold means 106. The drug conduit 108 will convey dispensed drug, including flushing and saline solutions, to be delivered to the target tissue 110 from the drug reservoir means and dispenser mechanism 104 to the manifold means 106. FIG. 1 is schematic and representative only, and the invention encompasses delivery of more than one drug via manifold means 106 which associates the drug or other substances with the laser delivery means located at any place within the physician's armamentarium.

Figure 2:
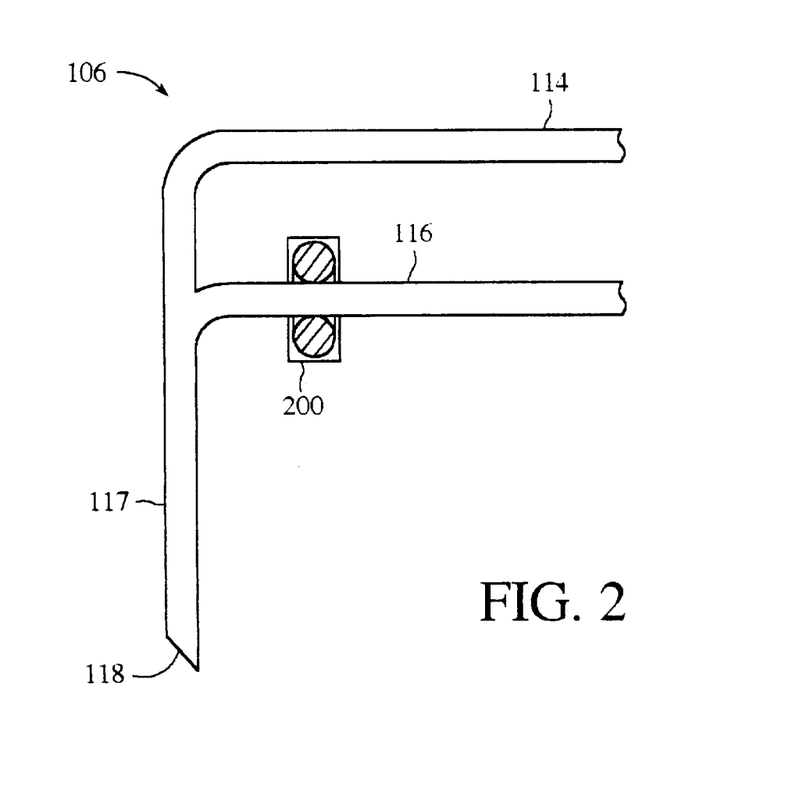
FIG. 2 is a representative side view of a preferred embodiment of the manifold means of the laser assisted drug delivery apparatus of the present invention.

FIG. 2 is a representative side view of a preferred embodiment of the manifold means 106 of the laser assisted drug delivery apparatus of the present invention. As will be evident by the drawings and disclosure herein, drug to be delivered to a target region in the human body flows from drug conduit 108 into a drug inlet 114 of the manifold means 106 of the present invention. The distal end 112 of the laser delivery means enters the laser inlet 116. Fluid seal 200 will prevent backflow through the laser inlet 116 of drug, solutions or other substances.

The manifold means 106 preferably terminates in tubular, common tube 117 having an aperture, or optionally, a hollow, slant-cut tubular surgical or other needle tip 118. This tip 118 can be formed from the same material as used for the manifold means 106, or another material, such materials in general including but not limited to tantalum, stainless steel, glass, etc. It will be understood that when employing either a percutaneous approach or a surgical approach, a tip 118 at the distal end 112 of the laser delivery means 102 can be used initially to pierce a surface of the target area. For TMR procedures, this will minimize bleeding from the epicardium, improve visibility in the region and reduce the incidence of adhesions between the epicardial surface and the pericardial sac. Furthermore, in a catheter assembly used in a vascular approach, such piercing will stabilize the device, for example on the surface of the heart or from within a heart chamber. The piercing mechanism may be angled fibers and suction may also be used at the target surface, with or without a piercing mechanism.

The common tube 117 shown defines a single lumen but it will be understood by those skilled in the art that more than 1 lumen may be included and that the common tube is designed to dispense drugs at the delivery site of the laser energy.

Then, advancing a fiber or other laser delivery means, with or without piercing tip 118, a predetermined distance into tissue such as myocardium and delivering laser energy will create an opening such as a TMR channel or other treatment site for delivery of drug therein. Retrolasing, as discussed below, can also be performed with the methods and apparatus of the present invention. Furthermore, it will be understood that the manifold means 106 embodiment described herein as a bifurcated or multifurcated needle is only representative of various such devices possible and considered within the scope of this invention. For example, and not to be construed in limiting in any way, additional configurations for the needle include wye ("Y") and vee ("V") shapes, etc.

Figure 3:
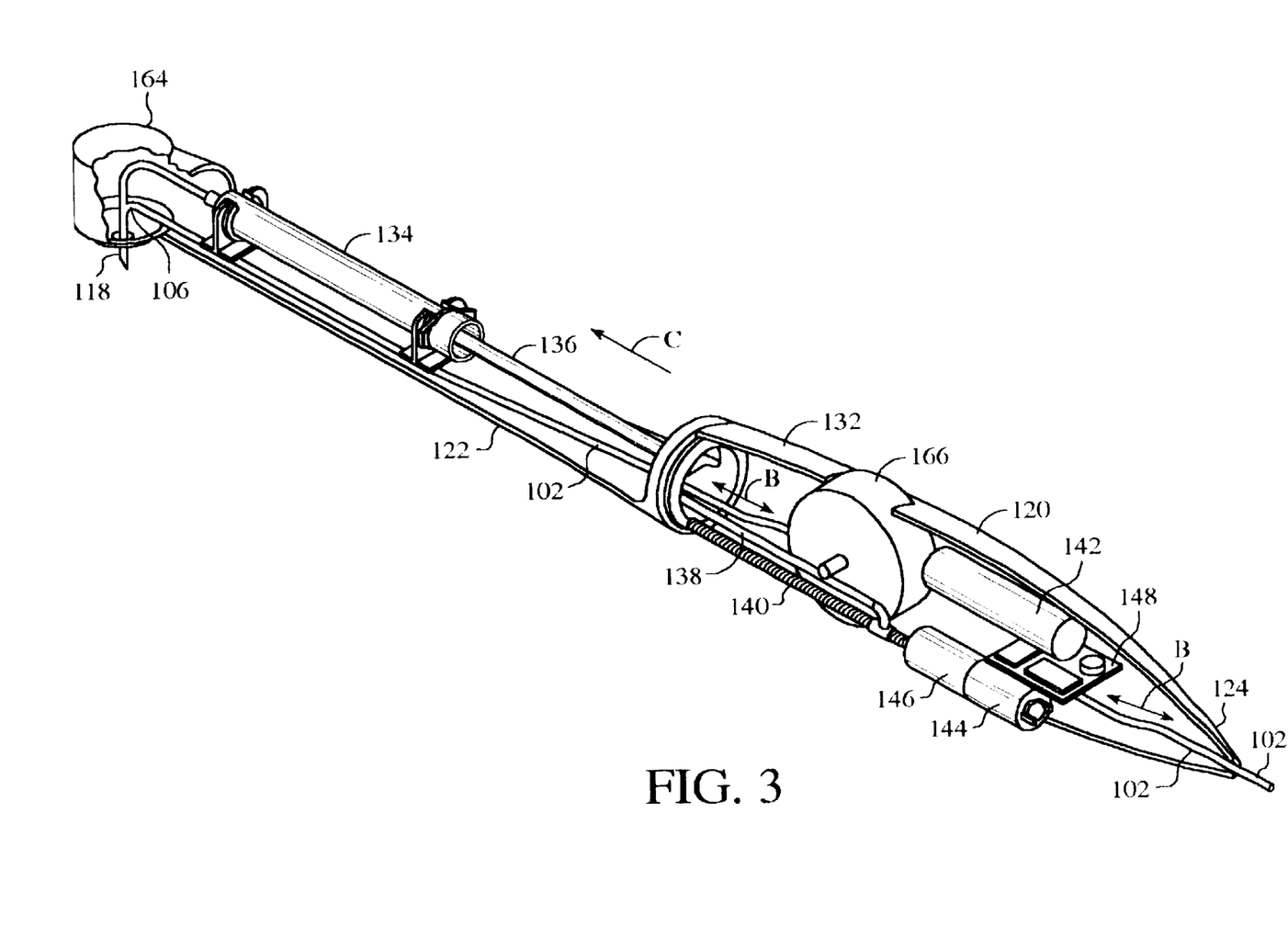
FIG. 3 is a representative isometric view of a preferred embodiment of the laser assisted drug delivery apparatus of the present invention.
Figure 6:
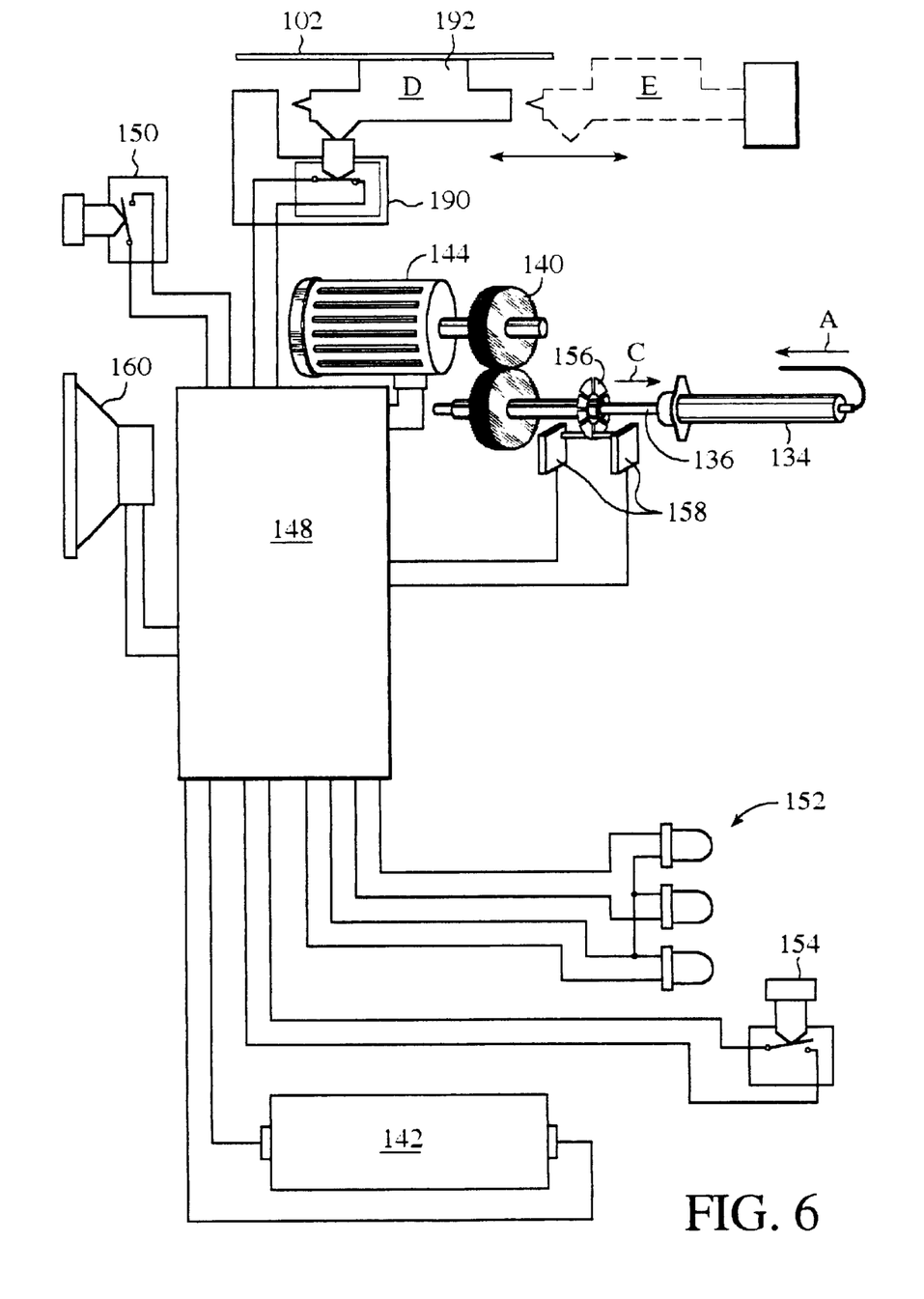
FIG. 6 is a representative electronics block diagram of a preferred embodiment of the laser assisted drug delivery apparatus of the present invention.

FIG. 3 is a representative isometric view of a preferred embodiment of the laser assisted drug delivery apparatus of the present invention. In these embodiments, the laser assisted drug delivery apparatus includes an elongated housing 132. The housing 132 of the apparatus defines a handle portion 120 and a neck portion 122. The housing 132 contains means for controllably dispensing, in precise amounts as desired, drug contained within the one or more reservoir means 134. Preferred embodiments of the apparatus further include laser delivery means advance means 166. As shown, the means for controllably dispensing such substances includes a drug reservoir 134, in this case a type of syringe. A piston, plunger or pellet dispenser 136 is moved axially by lead arm 138, driven by lead screw 140. A power source 142, such as a battery, powers a small motor 144, which is coupled to the lead screw 140 by means of gearhead 146. In a preferred embodiment, a stepper motor is used. The motor 144 is actuated by signals generated and received by controller 148, for example electronics mounted on a printed circuit board. A dispense button 150, as shown in FIG. 6, when manually depressed, will dispense at least one aliquot of drug. It will be understood that the controller and logic thereof may also be programmed to dispense a series of aliquots, at predetermined time intervals or according to other parameters, into the manifold means 106 from drug conduit 108.

FIGS. 4A–4D are representative views of a preferred embodiment of a dispenser apparatus with magazine-type manifold of the present invention. Drug unit, pellet, capsule or other solid or semi-solid 210 is stored within drug inlet 114. The stack of drug units or other drug solid 210 is urged forward by spring member 212. Blocking member 214 prevents the forward most drug unit 210 from entering the common tube 117 and tip 118 when the distal tip 112 of laser delivery means 102 is not extended through the manifold means 106.

Figure 4A:
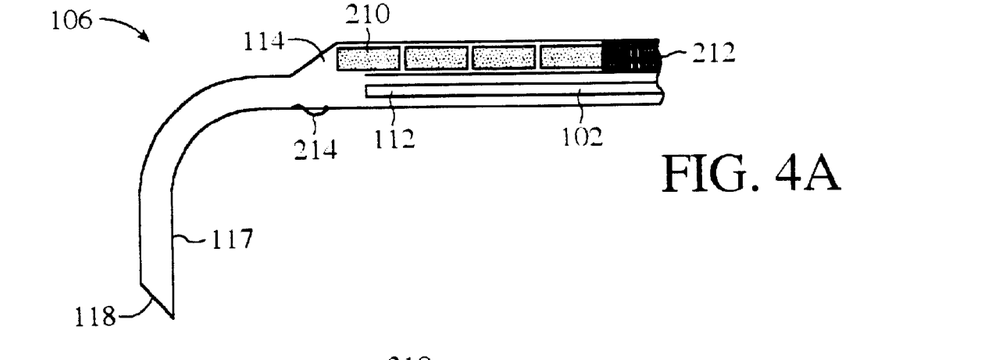
FIGS. 4A–4D are representative views of a preferred embodiment of a dispenser apparatus with magazine-type manifold of the present invention.
Figure 4B:
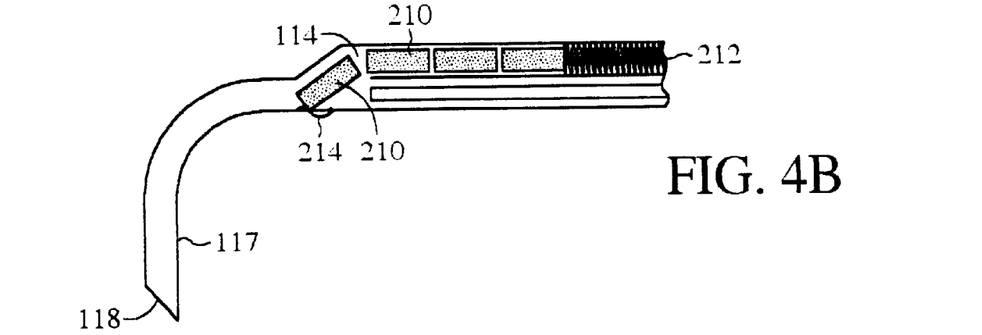
Figure 4C:
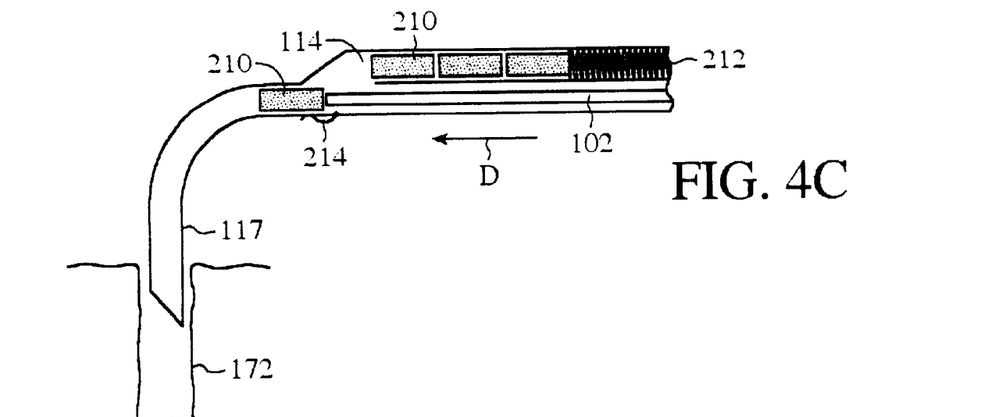
Figure 4D:
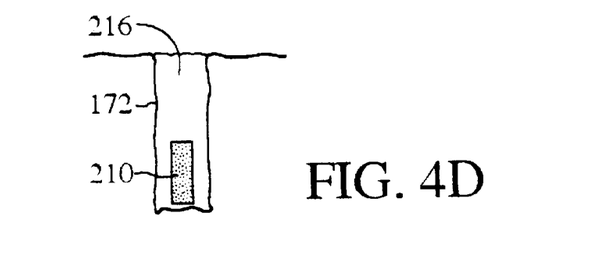

Thus, as shown in FIGS. 4A–4D, the distal end 112 of laser delivery means 102 is extendable through manifold means 106 and through common tube 117 and tip 118. A TMR channel or other laser and/or mechanically created opening 172 can be formed in tissue by advancing the distal tip 112 of laser delivery means in direction D. Thereafter, laser delivery means can be retracted, thus allowing the forward most drug solid 210 to be loaded into manifold means 106 where it will be held in place as shown by blocking member 214. It will be understood that the mechanical apparatus shown for dispensing such drug units can be modified to include optical sensors, step motors, etc., and will be included within the scope of the present invention. As shown in FIGS. 4C and 4D, as laser delivery means is advanced again, the distal end 112 of laser delivery means will act as a push rod and will cause drug solid 210 to be dispensed through tip 118 and deposited within opening 172. The opening may then seal 216 or be sealed naturally or otherwise.

Figure 5A:
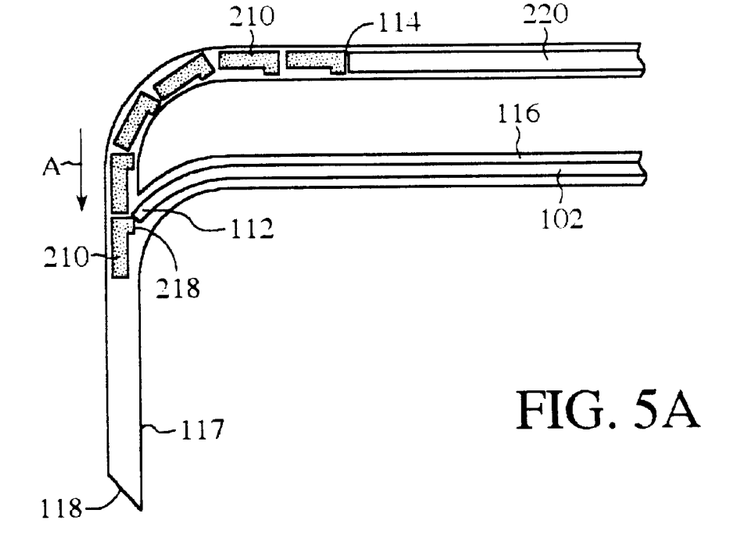
FIGS. 5A–5B are representative views of a preferred embodiment of a dispenser apparatus with magazine-type manifold of the present invention.
Figure 5B:
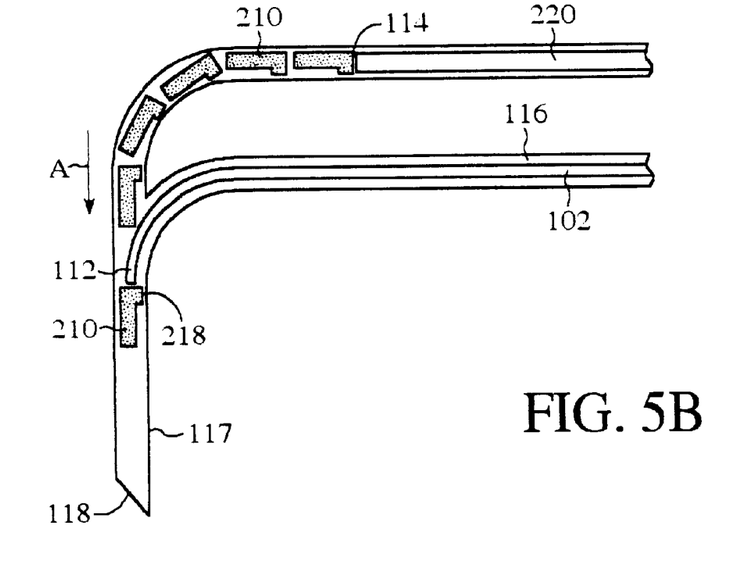

FIGS. 5A and 5B are representative views of a preferred embodiment of a dispenser apparatus with magazine-type manifold of the present invention. Drug solids 210 each having a small end section 218 are used. Such drug solids 210 will be pushed by plunger 220 into common tube 117 and through tip 118. The plunger 220, push rod, spring mechanism, optical switch, etc., alone or in conjunction with other apparatus, will advance the forward most or distal most drug solid into place. Then, once laser delivery means 102 is advanced, distal end 112 will engage the end section 218 of drug solid 210 thereby advancing it as well, as shown in FIG. 5B. As above, drug solid 210 can be dispensed and deposited as desired, for example, within blind or dead-end TMR channels, open-ended channels, etc. It will be understood that numerous other embodiments of the drug unit advance mechanism are possible and will all be considered within the scope of the method and apparatus of the present invention.

It will be understood that, with regard to recent advances in the field of TMR, various TMR means are known. Such TMR means will include, and are not limited to, finger tip devices, guide block devices, J-grip handpieces, etc. Such handpieces, with features including but not limited to fiber advance means, depth stop adjust means, rotation control means to form dual and multiple channels from a single opening, as well as other auxiliary control mechanisms, are more fully described in co-pending U.S. patent applications Ser. No. 08/675,698 and Ser. No. 08/675,732, both filed Jul. 3, 1996, as well as Ser. No. 08/664,956 filed on Jun. 13, 1996.

With regard to FIG. 3 and the other figures, a preferred embodiment of the present invention for use in surgical and minimally invasive surgical (MIS) procedures includes, as shown, a head portion 164 which is placed against or adjacent the exterior of the heart to be revascularized or otherwise treated. A laser delivery means 102 enters the rear portion 124 of the housing 132 and is movable as shown in direction B therein. It will be understood that the laser delivery means 102 may also be retracted in the opposite direction therethrough. A thumbwheel or other laser advance means 166 is used to automatically advance the distal end 112 of the laser delivery means 102 for forming a plurality of TMR channels into which drug can be deposited prior to, simultaneously with, and/or subsequent to said forming.

In operation, once the drug reservoir is charged with a drug as described above, or a saline or other flushing solution for flushing, cooling and/or otherwise treating the laser created openings such as TMR channels, the piston 136 will be positioned in an extended position, as shown. When actuated, the piston 136 will be driven in direction C. Resultant flow of metered quantities of drug will be through drug conduit 108 and into the drug inlet 114 of manifold means 106. From there, drug flow is through tip 118 and either directly into the opening 172 or into opening 172 surrounding laser delivery means 102. (See FIG. 7)

A preferred embodiment of the drug delivery apparatus 104 can include any of a wide range of drug reservoirs. Typical reservoir 134 volumes are 1, 2 and/or 3 milliliters. Typical aliquots, as integral fractions of a complete piston stroke, for dispensing in an automated manner, i.e. upon activation of some button or switch which would at least initiate drug flow and then either continue until released or otherwise deactivate or continue for a predetermined time or volume of delivery, are $\frac{1}{30}$, 1.50, $\frac{1}{100}$ and $\frac{1}{300}$ of the entire reservoir volume. By selecting specific reservoir volume, aliquot fractional amount and control of drug or other substance concentration within said drug reservoir, essentially any preselected volume or other amount of drug or other substance can be accurately delivered hereby. A selector means such as a selector switch (not shown), optionally located in housing 132 may be provided for such user settings selection. A clear plastic door covering such selector means provides immediate information to the operator of the apparatus as to current settings and helps prevent undesired and/or unintentional parameter adjustments.

Another beneficial aspect to the present invention is the ability to use the apparatus for flushing and cooling. Saline solution and blood, as well as solutions containing drugs or other specific compounds, can all be controllably dispensed through the apparatus of the present invention.

Therefore, it will be apparent to those skilled in the art that, with regard to FIG. 1, the method and apparatus of the present invention include those systems in which the drug reservoir is on board as well as off board. Reservoirs containing drug, flushing or cooling solutions, etc., could be maintained at some convenient place within the armamentarium of the procedure connected to the apparatus of the present invention with tubing, etc. It is also convenient to provide an apparatus with connections to one or more reservoirs external to the apparatus as well as to one or more reservoirs on-board, as shown.

FIG. 6 is a representative electronics block diagram of a preferred embodiment of the laser assisted drug delivery apparatus of the present invention. It will be understood that the following is representative of a single embodiment of the present invention, a large number of additional preferred embodiments will be readily apparent and included within the scope of the present invention.

Fiber advance activation means includes a switch means 190 such as thumbwheel 166. Switch means 190 switches power from power source 142 to fiber advance mechanism 192 to advance laser delivery means 102 in direction B by fiber advance mechanism 192. Thumbwheel 166 or other fiber advance means will be operative through a given angular range, for example 60°±15°. Switch means 190 also comprises, in a preferred embodiment, an audible indicator, such as a beeper, to indicate to the operator fiber position— as an example, a first beep or set of beeps indicating a retracted position, and other beeps or sets of beeps indicating other positions including a fully advanced position, a position 5 millimeters or more or less before a hard stop, etc.

Power source 142 will permit illumination of one or more of a plurality of indicators, including aliquot size indicator lights 152. Aliquot size selection means 154, typically a toggle or push button type switch, will permit the user to verify and/or select the size of the aliquot to be operatively dispensed.

Based on the foregoing, it will be understood that drug delivery is initiated, in a preferred embodiment of the present invention, by manual activation of dispense activation means 150, such as a toggle or push button, make and break switch, etc. Such dispense activation means 150 will send a signal directly to controller 148 to dispense one or more aliquots in a predetermined time period. Controller 148 will actuate motor 144 so as to cause rotation of lead screw 140. Optical flag 156, configured to rotate in unison with lead screw 140, will allow detection of rotation of lead screw 140 by sensors 158. Such sensors may include infrared LED sensors, motion sensors, etc. As rotation occurs, piston 136 is driven toward drug reservoir 134 in direction C, thus dispensing a predetermined amount of drug, drug solution in direction A through drug conduit 108 into manifold means 106. Completion of a dispense cycle, i.e. dispensing of either one or more individual aliquots, will be audibly indicated by cycle complete indicator means 160. Such cycle complete indicator means 160 could comprise a beeper to produce a beep or series of beeps or other audible sounds, or to activate indicator lights, etc. Such cycle complete indicator means 160 could also be configured and/or actuated to indicate an empty drug reservoir, other transient or set operation parameters apparatus diagnostics, etc.

Figure 7:
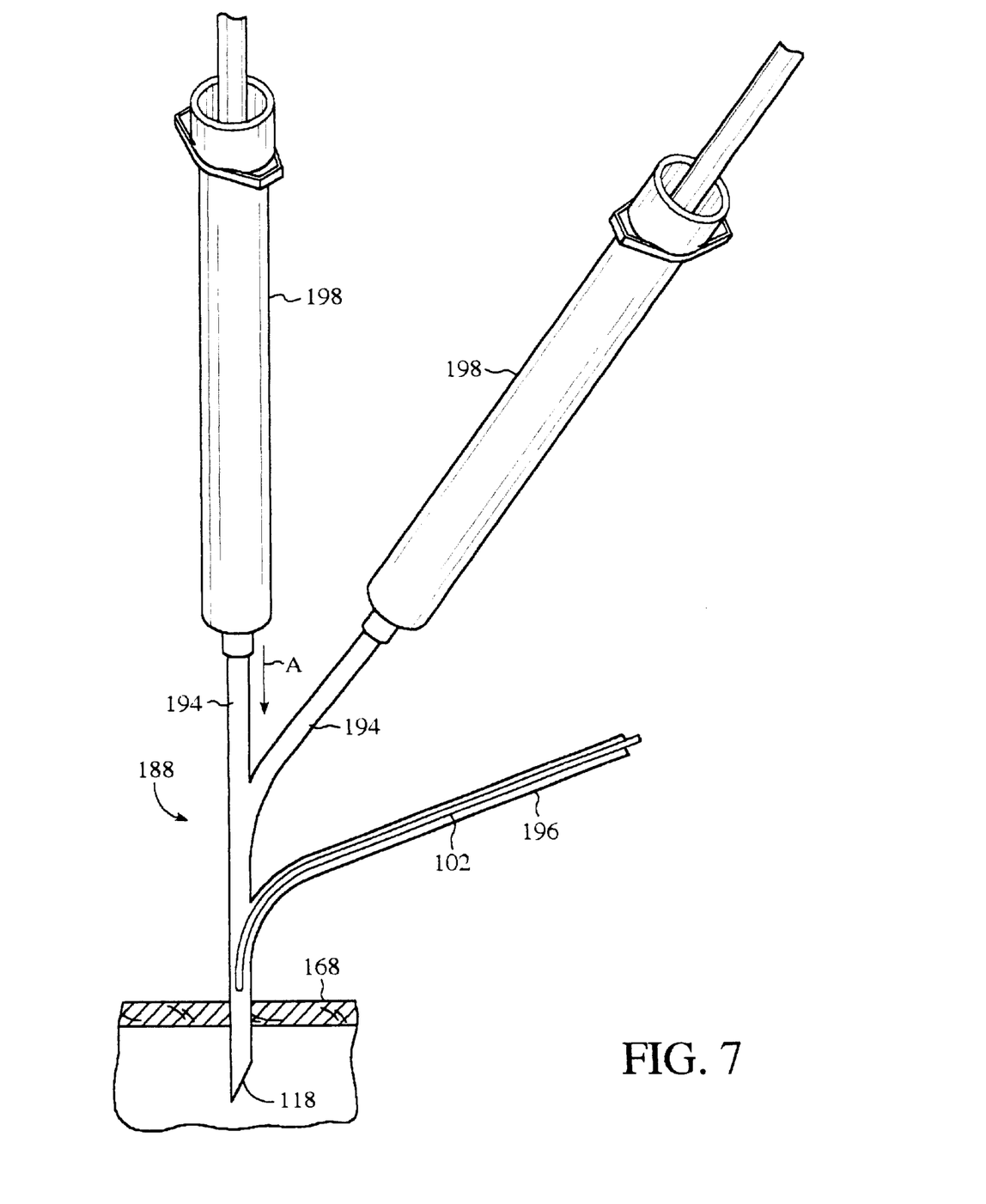
FIG. 7 is a representative view of a preferred embodiment of a multifurcated manifold means of the laser assisted drug delivery apparatus of the present invention.

FIG. 7 is a representative view of a preferred embodiment of a multifurcated manifold means 188 of the laser assisted drug delivery apparatus of the present invention. A plurality of drug inlet branches 194 as well as a laser delivery means 102 inlet branch 196 comprise the multifurcated manifold means 188. It will be understood that the multifurcated manifold means 188 is shown diagrammatically, and that numerous embodiments for such manifold means are possible. The laser assisted drug delivery apparatus of the present invention could include a plurality of drug reservoirs, including saline solution, for flushing the device, flushing TMR channels or other laser created openings, or to deposit one or more different drug solutions or other substances therein. Such apparatus would also contain a plurality of drug reservoirs 198, each situated either proximal to or distal to the main housing of the apparatus of the present invention, each with its own corresponding drug inlet channels 194, and a plurality of separate dispense activation buttons and associated piston, etc., or other internal configuration allowing for selectively dispensing such plurality of drug solutions, saline flush, aspiration solution or other substances.

Method of Use

Figure 8:
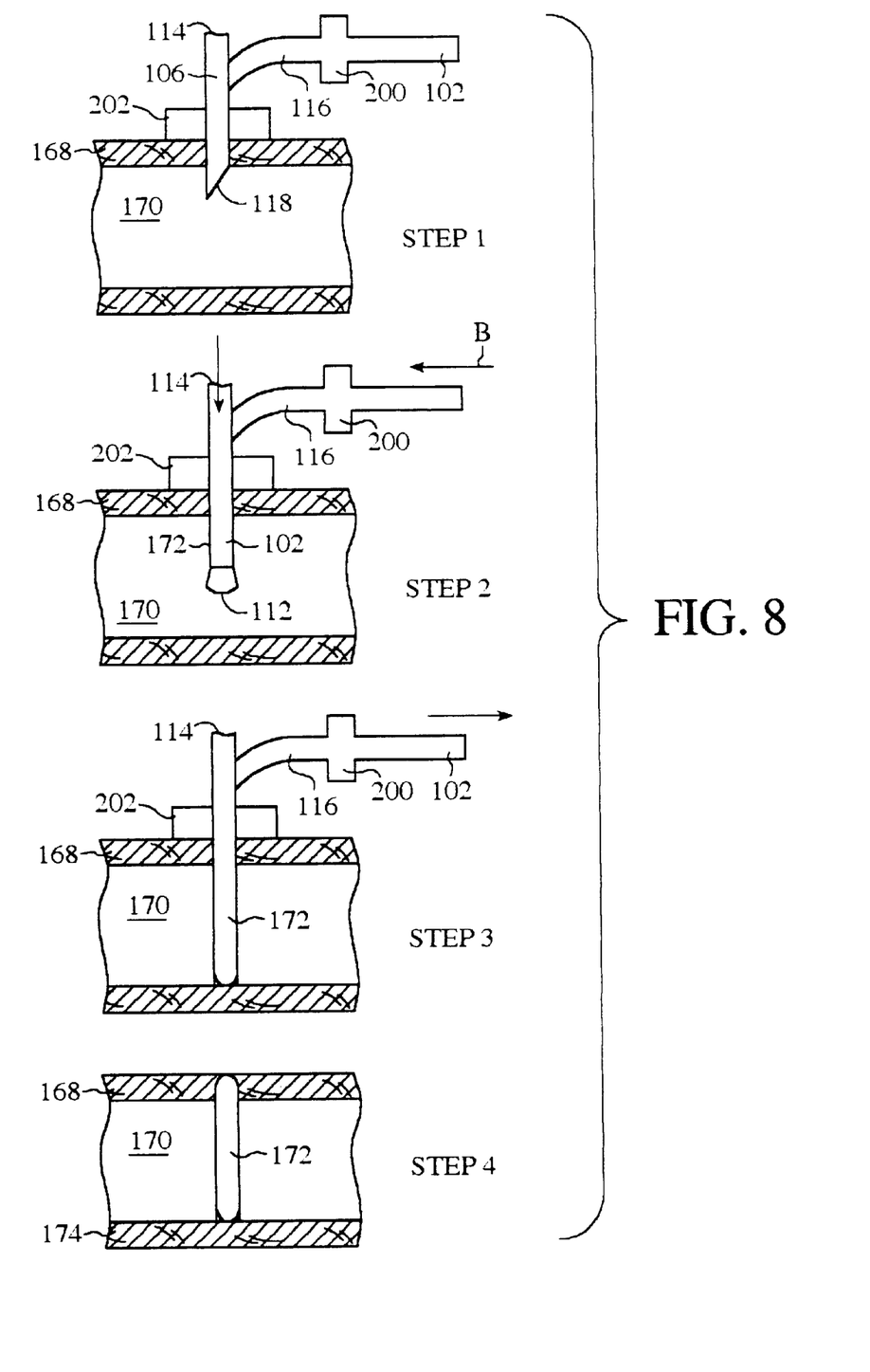
FIG. 8 is a representation of the steps of a method of use of the laser assisted drug delivery apparatus of the present invention.

FIG. 8 is a representation of the steps of a method of use of the laser assisted drug delivery apparatus of the present invention. Step 1 shows tip 118 of manifold means 106 inserted into first surface 168. It will be understood that the first surface 168 can be an epicardial surface, an endocardial surface, or other structure within the human body in which a drug is to be delivered. It will be understood that fluid seal 200 can be located either within or adjacent drug inlet 114 and/or within or adjacent laser inlet 116. Such fluid seal means 200 typically include a compressible rubber or other material gasket or stopper arrangement. A guide block 202, or other head such as head 164, serves to maintain the device and the manifold means stationary with respect to surface 168, with or without suction.

In step 2, a TMR channel or other laser created opening 172 is formed by extending the distal end 112 of laser delivery means 102 through the laser inlet 116 and the tip 118 of the manifold means 106. The TMR channel or other laser created opening 172 can terminate at a point within myocardium 170 or can pass entirely through the structure and a second surface 174. The second surface 174 could likewise be either an endocardial surface or other structure defining surface within the human body. It will be understood that during this step, i.e. as the opening 172 is being formed, drug can be dispensed through the first inlet channel 114 for deposit within the opening 172, in this case the drug will flow around and/or surround the distal end 112 of laser delivery means 102.

In step 3, laser delivery means 102 is retracted from opening 172. As before, at this point drug may be dispensed through the drug inlet 114 of manifold means 106 for deposit within opening 172. In step 4, the tip 118 and guide block 202 is removed, leaving a TMR channel or other laser created opening 172 behind, typically containing dispensed drug solution or other substances therein.

FIGS. 9A–9F are representative channel diagrams and regions of drug delivery therein possible with the laser assisted drug delivery apparatus of the present invention. As described, a single TMR channel or other laser created opening 172 can be formed with the present invention. Such opening can originate from any first surface 168 of essentially any structure within the human body. A wye ("Y") shaped TMR channel or other laser created opening 176 can also be formed. In this case, it is particularly advantageous to deposit drug at or near the branch 178 of the wye ("Y") shaped opening 176. It will be understood that such drug could in reality be deposited at essentially any point within the wye ("Y") shaped opening 176. Similarly, in the case of a vee ("V") shaped TMR channel or other laser created opening 180, drug solution or other substance can be deposited at essentially any point therein.

Figure 9A:
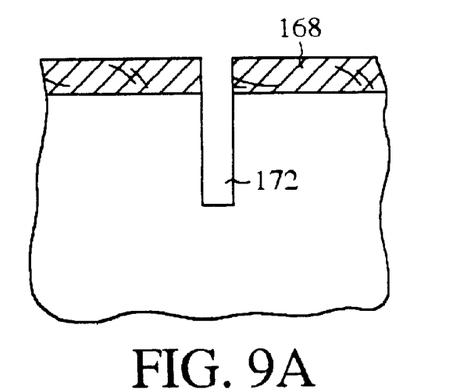
FIGS. 9A–9F are representative channel diagrams and regions of drug delivery therein possible with the laser assisted drug delivery apparatus of the present invention.
Figure 9B:
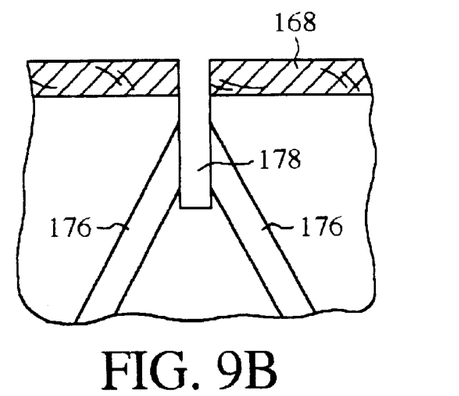
Figure 9C:
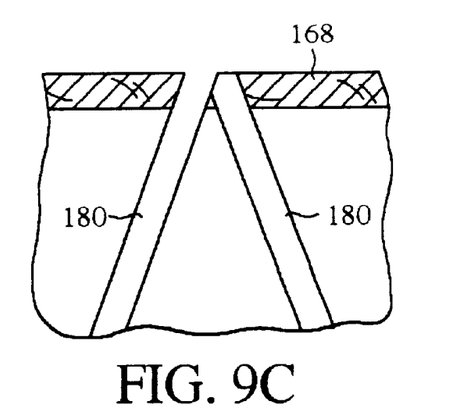
Figure 9D:
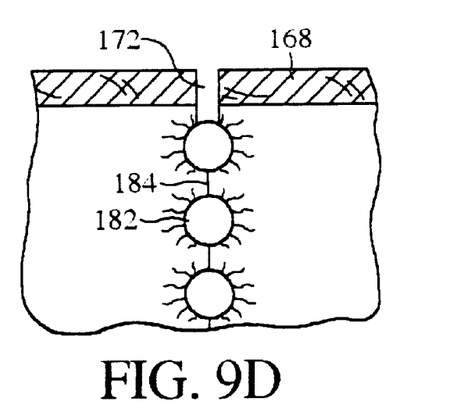
Figure 9E:
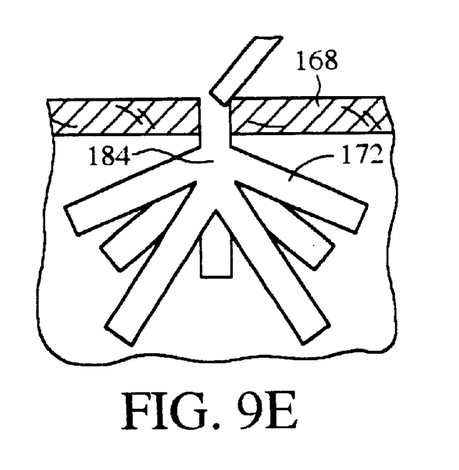
Figure 9F:
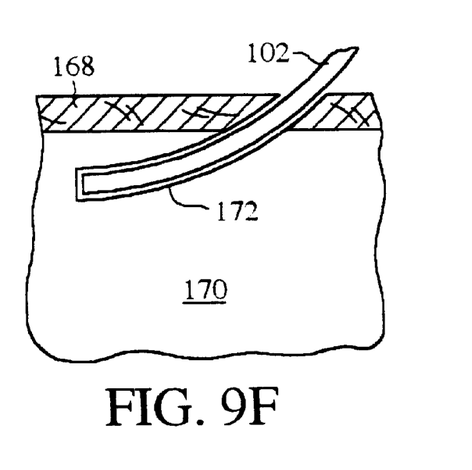

It will be noted that FIGS. 9A, 9E and 9F show "blind" or dead-ended channels. As made clear by the foregoing, these types of channels will be especially suited for drug delivery, especially with regard to drug solids, pellets, time release formulations, etc. Such channel patterns can be created often by making a single opening at the surface, creating a first channel in a first, predetermined angle, retracting the laser delivery means and reorienting the laser fiber or the device so as to form one or more subsequent channels at different angles to each other. FIG. 9F shows a TMR channel created just a short distance below and essentially parallel to the surface of the tissue. Such revascularization just below the typically 1–3 millimeter boundary layer of surface capillaries will encourage their growth downward into muscle, deeper myocardium or other parts of the tissue.

It will be understood that while the present invention has been described for performing TMR procedures, the apparatus and methods described herein are equally intended for use in any suitable procedure in which drugs are to be deposited into portions of the body using laser energy to gain access to the depository site. Another procedure known as "stimulation", for example, is performed by using laser energy to create zones or pockets 182, optionally interconnected at least initially by interconnecting channels 184 ablated through the tissue, for the introduction of blood born growth and healing factors and stimulated capillary growth surrounding the lased zones or pockets to create an increased supply of oxygen to the tissue and thus a revitalization of the heart muscle or other body tissue. Drugs, solutions or other substances can be deposited into the zones or pockets. Methods and apparatus for causing stimulation are more fully described in co-pending U.S. patent application Ser. No. 08/664,956 filed Jun. 13, 1996.

Alternatively, retro-lasing can also be performed using the apparatus and methods of the present invention. This novel use includes the steps of advancing a fiber or other laser delivery means, preferably with a tip a predetermined distance into the myocardium and then delivering laser energy to create a TMR channel or other treatment site while retracting the fiber, laser delivery means or other functional device. Therefore, with regard to TMR, inasmuch as laser energy is only delivered during retraction of the fiber, the possibility of advancing the fiber too far and lasing through the epicardium is eliminated, as are complications arising from such epicardial perforations including but not limited to cardiac tamponade (a buildup in the pericardial sac of an excess of fluid such as blood), proliferation of adhesions, etc. However, with regard to drug delivery, drug solutions or other substances can be deposited at essentially any operative time within the procedure, either during piercing, after piercing, during retro-lasing or at some point thereafter.

Adjunct use of appropriate blood seal means, depth stop apparatus such as clamps, etc., visualization means, marker means as well as other hardware and methodology will be considered within the scope of the present invention. Visualization can be enhanced with ultrasound or by using radio-opaque materials for construction, metal or other material foils or bands, especially at or adjacent distal ends of the optical fibers or as part of the drug solution formulations themselves. This will assist the practitioner in fluoroscopy or other visualization methodology for precise and accurate positioning of the apparatus and deposit of drug solutions and other substances. Additionally, visualization will also be useful to the physician for observing the drug delivery process and/or the drug activity within the channel or pocket.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, rods, cables, articulated arms, mirrors configurations and other laser delivery means with and without focusing lens and the like. It will also be understood that the apparatus and method of the present invention as described herein, including the novel combination or use with of any conventional mechanism or method which are known to those skilled in the art, are included within the scope of this invention.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A method for dispensing solid and semi-solid drugs into tissue comprising:
    (a) providing a drug dispensing device having a tube with proximal and distal ends and at least one lumen, the distal end of the tube having a tissue piercing device surrounding an opening which communicates with the at least one lumen, and a drug dispenser mechanism advanceable into the at least one lumen;
    (b) loading at least one solid or semi-solid drug unit into the at least one lumen;
    (c) positioning the distal end of the tube on the tissue;
    (d) piercing the tissue with the tissue piercing device to form an aperture in the tissue;
    (e) extending a distal end of a laser delivery means through the at least one lumen and through the aperture in the tissue forming a first laser-created opening in the tissue;
    (f) operating the drug dispenser mechanism to advance a first of the at least one solid or semi-solid drug unit within the at least one lumen into the distal end of the tube; and
    (g) operating the drug dispenser mechanism further to move the first of the at least one solid or semi-solid drug unit through the opening and into the first laser-created opening in the tissue.

2. The method of claim 1 wherein the drug delivery device further comprises a blocking device within the at least one lumen, step (f) of the method further comprising the step of ceasing to advance the drug dispenser mechanism after the first of the at least one solid or semi-solid drug unit is pushed past the blocking device by the drug dispenser mechanism.

3. The method of claim 1 wherein the drug delivery device further comprises a blocking device within the at least one lumen, the method further comprising the step of blocking delivery of additional solid or semi-solid drug units of the at least one solid or semi-solid drug unit in the absence of advancement by the drug dispenser mechanism.

4. The method of claim 1 wherein steps (e) and (g) occur simultaneously.

5. The method of claim 1 further comprising the step of:
    retracting the distal end of the laser delivery means from the at least one lumen before performing step (g).

6. The method of claim 1 wherein step (e) further comprises:
    retracting the distal end of the laser delivery means from the at least one lumen; and
    extending the distal end of a laser delivery means through the at least one lumen and through the aperture in the tissue forming a second laser-created opening in the tissue, wherein the first and second laser-created openings form a wye, and further wherein the first of the at least one solid or semi-solid drug unit is moved into a branch of the wye.

7. The method of claim 1 wherein step (e) further comprises:

retracting the distal end of the laser delivery means from the at least one lumen; and extending the distal end of a laser delivery means through the at least one lumen and through the aperture in the tissue forming a second laser-created opening in the tissue, wherein the first and second laser-created openings form a vee, and further wherein the first of the at least one solid or semi-solid drug unit is moved into any point in the vee.

8. The method of claim 1 wherein step (e) further comprises:

performing a stimulation procedure with the distal end of the laser delivery means wherein the laser-created opening forms at least one pocket having an interconnecting channel, and further wherein the first of the at least one solid or semi-solid drug unit is moved into the at least one pocket.

9. The method of claim 1 wherein the laser-created opening is a dead-ended channel.

10. The method of claim 1 wherein the laser-created opening extends through the tissue forming an open-ended channel.

11. The method of claim 1 wherein step (e) further comprises:

retracting the distal end of the laser delivery means from the at least one lumen; and reorienting the distal end of a laser delivery means on the aperture of the tissue before forming at least two more laser-created openings at different angles from each other and the first laser-created opening, and further wherein the first of the at least one solid or semi-solid drug unit is moved into a branch of the first laser-created opening and the at least two more laser-created openings.

12. The method of claim 1 wherein the laser-created opening is created a short distance below and essentially parallel to a surface of the tissue.

\* \* \* \* \*